Figure 1:
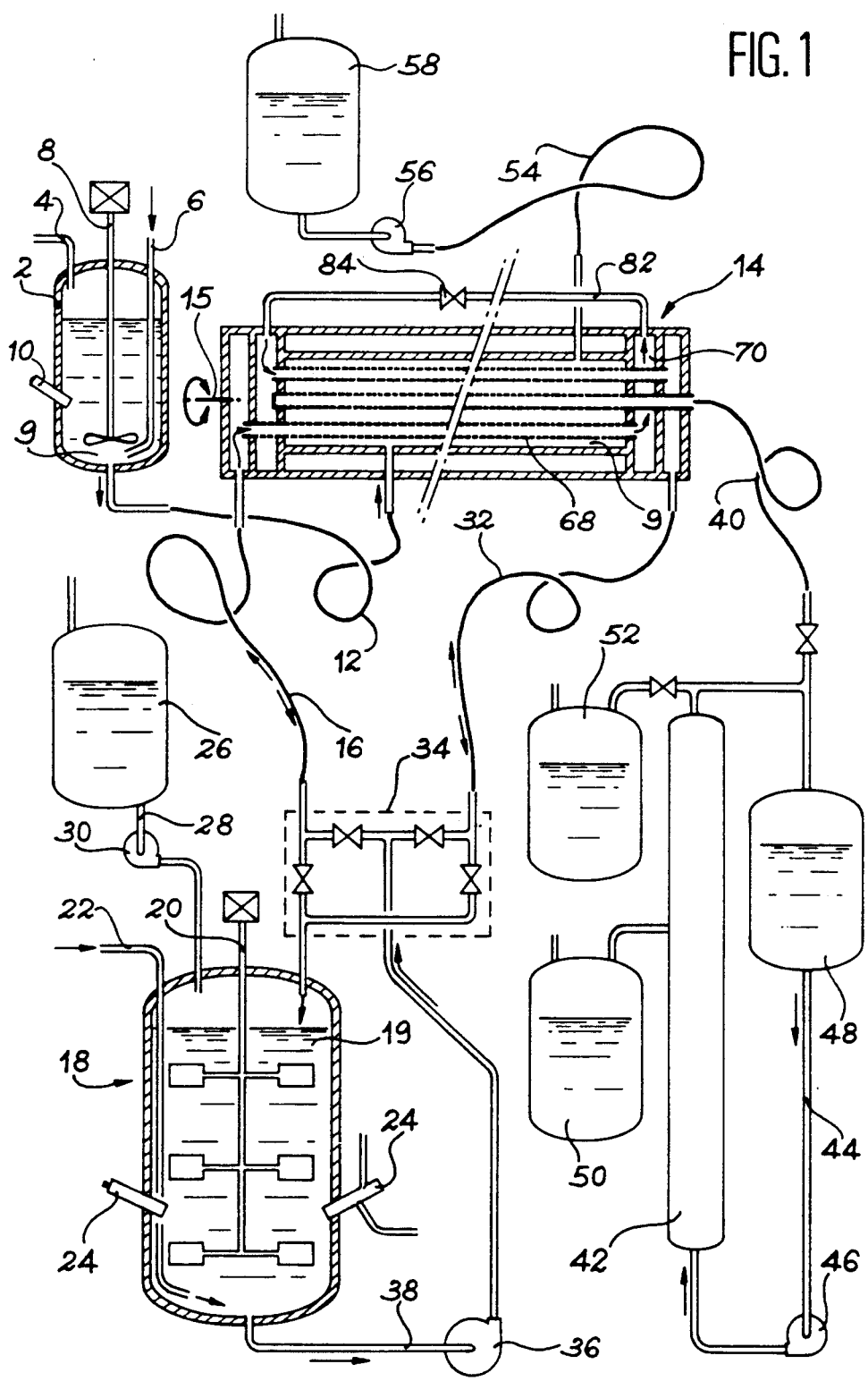

United States Patent [19]

Besnainon et al.

[11] Patent Number: 5,064,764
[45] Date of Patent: Nov. 12, 1991

[54] MINERAL HOLLOW FIBER BIOREACTOR FOR THE CULTIVATION OF ANIMAL CELLS

[75] Inventors: Bernard Besnainon; Marie-Paule Elluard, both of Aix-En; Pierre Lessart, Volx; Alain Philippe, Pertuis, all of France

[73] Assignee: Commissariat A l'Energie Atomique, Paris, France

[21] Appl. No.: 555,436
[22] PCT Filed: Dec. 19, 1989
[86] PCT No.: PCT/FR89/00664
§ 371 Date: Aug. 13, 1990
§ 102(e) Date: Aug. 19, 1990
[87] PCT Pub. No.: WO90/06990
PCT Pub. Date: Jun. 28, 1990

[30] Foreign Application Priority Data

Dec. 20, 1988 [FR] France ................. 88 16851

[51] Int. Cl.$^5$ ............... C12M 3/00; B01D 63/00; B01D 36/00
[52] U.S. Cl. .................. 435/285; 435/310; 435/240.242; 435/813; 210/500.23; 210/500.25; 210/321.8
[58] Field of Search ............... 435/240.241, 240.242, 435/240.25, 283, 284, 813, 819; 210/323.2, 340, 500.23, 500.25, 497.01, 321.8, 321.79

[56] References Cited

U.S. PATENT DOCUMENTS

| 4,391,912 | 7/1983 | Yoshida et al. | 435/240.25 |
| 4,722,902 | 2/1988 | Harm et al. | 435/284 |
| 4,804,628 | 2/1989 | Cracauer et al. | 210/500.23 |
| 4,849,104 | 7/1989 | Garcera et al. | 210/340 |
| 4,874,516 | 10/1989 | Kondo | 210/497.01 |
| 4,938,931 | 7/1990 | Cussler | 435/284 |

FOREIGN PATENT DOCUMENTS 02379 4/1986 PCT Int'l Appl. .
02378 4/1986 World Int. Prop. O. ....... 435/240.25

Primary Examiner—David L. Lacey
Assistant Examiner—William K. Y. Chan
Attorney, Agent, or Firm—Pearne, Gordon, McCoy & Granger

[57] ABSTRACT

This bioreactor comprises two enclosures (60,62) connected by first and second porous carbon tube (66,68) for the circulation of the nutrient medium (19) and immersed in the culture medium (9), internal mineral, microporous membranes (70) located in each first and second tube for ensuring the passage of the nutrient medium to the culture mdium and whilst serving as a barrier for contaminants, external, mineral, microporous membranes (72) located outside each first and second tube for ensuring the passage of the nutrient medium to the culture medium and while serving as barrier for the cells and the proteins contained in the culture medium, at least one porous mineral tube (86) for the extraction of the substances produced by the cells, which is isolated from the two enclosures and equipped with an external, microporous, mineral membrane impermeable to the cells, but permeable to the macromolecules produced in the culture medium.

13 Claims, 3 Drawing Sheets

MINERAL HOLLOW FIBER BIOREACTOR FOR THE CULTIVATION OF ANIMAL CELLS

DESCRIPTION

The present invention relates to a bioreactor and to an apparatus for the continuous culture on an industrial scale of animal cells. It is applicable to the production of all animal cells and to the production of metabolites produced by the cells, such as e.g. monoclonal antibodies. The bioreactor and the apparatus according to the invention permit the culture under sterile conditions of animal cells, such as hybridomas.

Various bioreactors are already known, which can be used in the culture of free cells (non-adhering), like those described in EP-A-0 113 328, EP-A-0 112 155, U.S. Pat. No. 4,661,455, EP-A-0 155 237 and EP-A-0 112 154. In all these known bioreactors use is made of water-impermeable, but gas-permeable membranes, so as to ensure the necessary oxygen transfer for the development of any animal cell. During the size extrapolation of these reactors, the problem of transfer surfaces very rapidly occurs. For example, it is calculated that for a Braun-type reactor equipped with a stirred vessel and silicone, oxygen transfer tubes, 700 meters of tubing would be required for a 75 l fermenter. In addition, the last four documents referred to hereinbefore relate to reactors constituted by planar membranes suffering from the disadvantage of bringing about non-homogeneous transfers.

Moreover, there is no way in which it is possible to regulate and control the clogging of these membranes by the cultured cells. In particular, the first aforementioned document forces the passage of the solution containing the cells through membranes. The immediate result is a much larger transfer of substances, but a side effect is an increase in the transfer pressure and a compression of the polarizing layer which has formed on the membranes and this has the consequence of increasing the risk of said membranes becoming blocked.

Moreover, apparatuses based on the confinement of cells between two different membrane types, one used for supplying certain substrates to the cells and the others for extracting certain products, have no device for regulating and checking on an intermediate basis the pressure drop and consequently have membrane portions which are poorly used, the pressures being close to one another on either side of the said membranes in certain areas, which leads to a limited transfer, which does not permit a controlled, intense supply of the necessary nutrient substrates.

Moreover, the progressive clogging of the membranes leads to a simultaneous reduction in the transfers of all the nutrient substrates, but in often varying proportions, which is prejudicial to the checking of the concentrations over a period of time and makes it impossible for these reactors to operate in a satisfactory manner over long periods.

The invention specifically relates to a bioreactor and to an apparatus for the culture of animal cells making it possible to obviate the disadvantages referred to hereinbefore.

The present invention therefore relates to a bioreactor for the culture of animal cells comprising:

a cellular culture chamber, formed by a sleeve and facing walls of two enclosures, respectively the intake enclosure and the discharge enclosure, containing on each occasion the cells and the culture medium, each enclosure being provided with an internal partition subdividing said enclosure into a first and a second respectively internal and external chambers;

at least one first porous mineral tube connecting the external chamber of the intake enclosure to the internal chamber of the discharge enclosure and traversing said culture chamber for supplying nutrient medium to the culture medium, said first porous mineral tube having on its inner face a first microporous filtering membrane allowing the passage of molecules of the nutrient medium with an average or middle molecular weight, but stopping the macromolecules of a high molecular weight, and on its outer face a second microfiltering membrane permitting the passage of the low molecular weight molecules and serving as a barrier for the cells and most of the proteins present in the cellular culture chamber;

at least one second porous mineral tube connecting the internal chamber of the intake enclosure to the external chamber of the discharge enclosure, whilst traversing the cellular culture chamber from which it makes it possible to extract the low molecular weight metabolites, said second tube having on its outer and inner faces filtering membranes identical to those of the first porous mineral tube;

a connecting pipe between the two internal chambers of the intake and discharge enclosures, whose supplementary pressure drop has the effect of bringing about a better material transfer through the first and second porous mineral tubes and which, by bringing about a flow in the same direction of the nutrient medium through said first and second porous mineral tubes, makes it possible to improve the homogeneity of the bioreactor.

The term average or middle molecular weight molecules means molecules having molecular weights between 50,000 and 300,000 Daltons. Therefore the low molecular weight molecules have molecular weights below 50,000 Daltons and the high molecular weight molecules have molecular weights in excess of 300,000 Daltons.

According to the invention, the first filtering membrane also serves as a barrier to particles such as viruses, microorganisms, cellular debris and gels. The low molecular weight metabolites are in particular ammonium ions, carbon dioxide or lactate.

Advantageously, the connecting pipe between the two internal chambers is equipped with a regulating valve making it possible to adjust and check the pressure drop in said pipe and thus obtain a very substantially constant transfer over the entire length of said first and second porous mineral tubes.

The bioreactor can function discontinuously (non-renewed medium) or continuously. In the latter case, an improvement to the bioreactor consists of bringing about a passage through the culture chamber of at least one third porous mineral tube isolated from the two enclosures and having its outer face covered with a microporous filtering membrane, which is impermeable to the cells, but permeable to the macromolecules produced in the cellular culture chamber. These macromolecules can consequently be withdrawn during the operation of the bioreactor via a pipe connected to the open end of said third porous tube.

The microporous filtering membranes are preferably mineral membranes and in particular $Al_2O_3$, $TiO_2$ or $ZrO_2$ membranes, although it is also possible to use other mineral materials such as pyrolytic carbon. However, steam-sterilizable organic membranes, such as polyvinylidene fluoride membranes can also be used. The porous tubes supporting said membranes are preferably made from porous carbon or alumina, although it is also possible to use other materials such as fritted or woven ceramics or metals.

In order to limit the clogging or blocking of the membranes deposited on the faces of the first and second porous tubes and thus obtain substantially constant transfer characteristics throughout the culture period, means are provided for reversing the passage direction of the nutrient medium within said first and second porous tubes. Under these conditions, the transfer directions of the first and second tubes with respect to the cellular culture chamber are reversed and the intake enclosure becomes the discharge enclosure and vice versa.

The increase in the transfer flow rate of the first tubes to the cellular culture chamber and from the latter to the second tubes can be obtained by increasing the supply rate of the nutrient medium and/or by bringing about a pulsation of said supply flow and/or by reducing the opening of the regulating valve of the connecting pipe between the internal chambers of the intake and discharge enclosures, which brings about an increase in the pressure of the nutrient medium in the circuit upstream of the valve.

The homogeneity of the culture chamber can be improved by means permitting an alternating 180° rotation of said bioreactor about a longitudinal axis parallel to the porous tubes.

The invention also relates to an apparatus for the continuous culture of animal cells comprising a bioreactor as defined hereinbefore and which is connected to a reactor for checking and preparing the nutrient medium, via flexible and preferably silicone pipes, as well as means for the continuous or sequential extraction of the substances produced by the cells.

The invention is described in greater detail hereinafter relative to non-limitative embodiments and the attached drawings, wherein show:

FIG. 1 an overall diagram of an apparatus for the culture of animal cells according to the invention.

Figure 2:
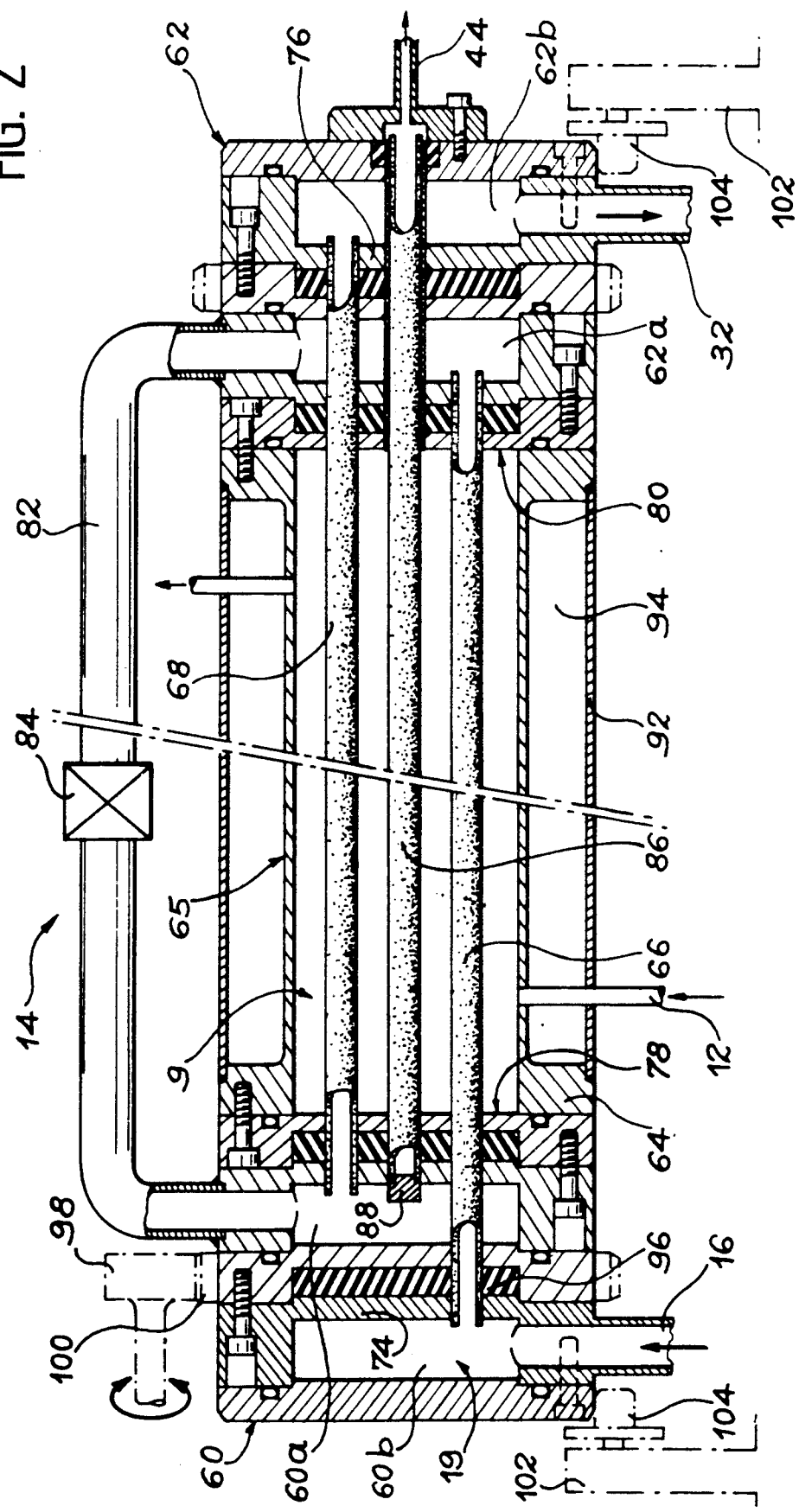

FIG. 2 in greater detail and in longitudinal section the bioreactor of the apparatus of FIG. 1.

Figure 3:
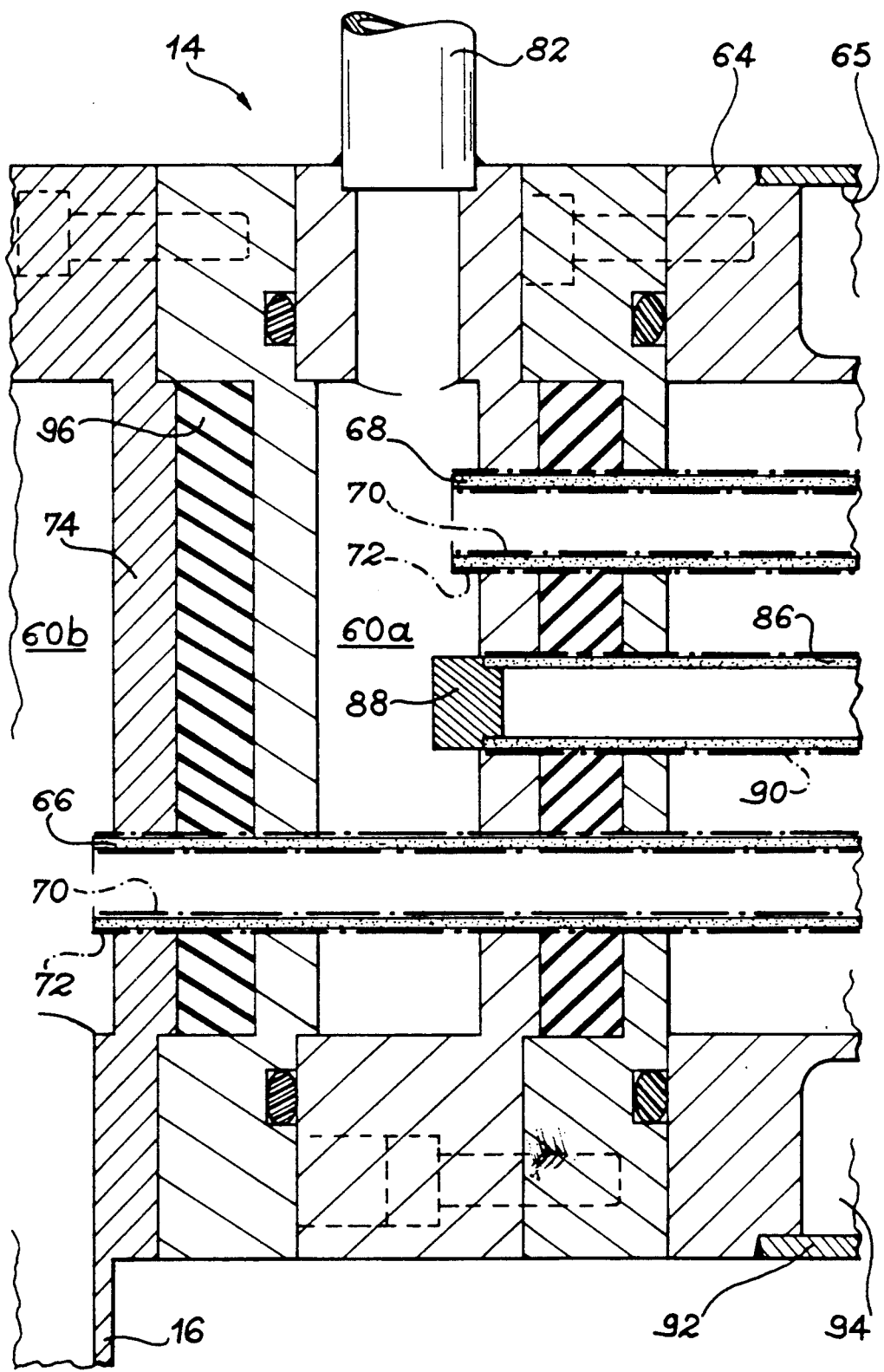

FIG. 3 a larger-scale part of FIG. 2 showing the different filtering membranes of the bioreactor.

With reference to FIG. 1, the apparatus for the culture of animal cells according to the invention comprises a vessel 2 for the preculture of animal cells and which is equipped with a $CO_2$ and air supply 4 and a nutrient solution supply 6, the gaseous mixture and the nutrient solution being necessary for the development of the animal cells contained in the culture medium 9. A stirrer 8 brings about a slow stirring of the culture medium 9. Sensors 10 for checking said medium and in particular the pH, the oxygen pressure and the dioxide pressure are provided. The vessel 2 and its equipment are used as the inoculum of the bioreactor.

The vessel 2 is connected via a flexible pipe 12 to a bioreactor 14 in which takes place the actual culture of the animal cells for the production of metabolites by said cells. The bioreactor has a longitudinal axis of symmetry 15.

The bioreactor 14 is equipped with a supply pipe 16 for the low molecular weight nutrient medium (below 50,000 Daltons) necessary for the life of the animal cells contained in the culture medium 9. This supply pipe 16 is flexible and is connected to an auxiliary reactor 18 for the preparation of the nutrient medium and for checking the latter.

The regulation of the pH, the oxygen pressure, the carbon dioxide pressure, the glutamine, the glucose and the amino acids of the nutrient medium takes place in said auxiliary reactor 18. The nutrient medium is 19 and it can be stirred by a system 20. The absence of proteins and cells in the reactor 18 makes it possible to use a violent stirring of the nutrient medium 19 (the shear stresses not having a limiting nature) and there can be a high air and carbon dioxide flow rate (no abnormal foam formation). The air and $CO_2$ are introduced into the reactor 18 via the supply pipe 22. Like all the other pipes and containers of the apparatus, said reactor 18 is steam sterilizable in situ.

The reactor or mixing chamber 18 is equipped with a device 24 for taking sterile samples of the nutrient medium 19 ensuring a sequential or continuous taking of samples automatically injected into analysers connected to a data processing system controlling said nutrient medium 19. This system makes it possible to inject, as required, glucose, glutamine or amino acids stored in a tank 26 connected to the reactor or mixing chamber 18 via a pipe 28 equipped with a pump 30.

The sterilization system for the complete apparatus, as well as the checking of the culture medium and the nutrient medium in an automatic manner are well known in the art and will not be described in greater detail.

The bioreactor 14 is also equipped with a flexible discharge pipe 32 for the nutrient medium 19 connected to the reactor 18. A valve means 34 makes it possible to periodically reverse the flow direction of the nutrient medium in the bioreactor 14 so as to prevent any clogging thereof. A pump 36 mounted on a rigid pipe 38 for discharging the nutrient medium 19 from the reactor or mixing chamber 18 and connected to the device 34 ensures the circulation of the nutrient medium.

The metabolites produced by the cells in the bioreactor 14 are extracted therefrom via a flexible pipe 40 connected to an ultrafiltration system 42 ensuring the separation of the metabolites from the other products of the liquid medium. The passage of the latter into the system 42 is ensured via a supply pipe 44 connected to the pipe 40 and equipped with a pump 46 and a buffer tank 48. Tanks 50 and 52 ensure the collection of the ultrafiltration products; the tank 50 recovering the spent media and the tank 52 the metabolites.

In order to compensate the extraction at 40 of the proteins during the sequential sampling of the culture products, there is a pipe 54 for supplying protein solution to the reactor 14. This flexible pipe 54 is equipped with a pump 56 and comes from a container 58 containing the protein solution.

According to the invention, the pipes 12, 16, 32, 40 and 54 connecting the bioreactor 14 to the other components of the culture apparatus are flexible, so as not to prejudice the alternating rotary movement by approximately 180° of the bioreactor 14 about its longitudinal axis 15. This rotary movement associated with the reversal of the circulation direction of the nutrient medium in the bioreactor 14 prevents any sedimentation of the cells in the latter.

Obviously, said flexible pipes can be replaced by rigid pipes equipped with tight or sterilizable, rotary coaxial or semicoaxial couplings.

The bioreactor 14 according to the invention shown in greater detail in FIGS. 2 and 3 comprises two cylindrical enclosures 60 and 62 arranged in longitudinal manner and mounted at each end of an inner, cylindrical ferrule or sleeve 64 for containing the culture medium 9. First and second porous mineral tubes 66 and 68 and which are in particular made from porous carbon are located in the sleeve 64 and positioned along the longitudinal axis of the bioreactor 14, so as to link the enclosures 60 and 62.

These tubes 66 and 68 permit the circulation of the nutrient medium from reactor or mixing chamber 18 and are in contact with the culture medium 9 contained in the chamber 65 defined by the inner sleeve 64 and the facing walls 78, 80 of the two enclosures 60, 62.

According to the invention, each tube 66 and 68 is equipped with an inner, porous, filtering membrane 70 and an outer, porous, filtering membrane 72. These membranes 70 and 72 are microporous, mineral membranes and are in particular made from zirconia.

The inner, filtering membranes 70 bring about the passage of average molecular weight molecules of the nutrient medium 19 to the culture medium 9, but prevent the passage of viruses and corrosive products present and also other high molecular weight particles in the nutrient medium towards the culture medium. Therefore they constitute a pollution barrier. Their cutoff threshold is in particular approximately 0.08 micrometer.

The external, filtering membranes 72 permit the passage of the low molecular weight molecules of the nutrient medium to the culture medium, but their cutoff threshold is lower than that of the internal membranes 70. These external barriers 72 constitute an effective barrier with respect to most proteins and cells contained in the culture medium 9. The cutoff threshold of these external membranes 72 is in particular 10,000 Daltons.

The fact that the cutoff threshold of the internal, filtering membrane is higher than that of the corresponding external membrane means that the overall permeability of the tube-membrane assembly is not excessively reduced.

According to the invention, each of the two enclosures 60 and 62 is subdivided into two chambers, namely an internal chamber and an external chamber, by a partition perpendicular to the tubes 66 and 68. Partition 74 of chamber 60 defines an internal chamber 60a and an external chamber 60b and the partition 76 of the enclosure 62 defines two chambers, namely an internal chamber 62a and an external chamber 62b.

The tube 66 traversing the facing walls 78 and 80 of the two enclosures 60 and 62, as well as the partition 74 connects the external chamber 60b of the enclosure 60 to the internal chamber 62a of the chamber 62. In the same way, the porous tube 68 traversing the facing walls 78 and 80 of the two enclosures 60 and 62 and the partition 76 links the internal enclosure 60a to the external enclosure 62b.

The nutrient medium 19 which is rich in the elements necessary for the culture of the cells and coming from the bioreactor or mixing chamber 18 e.g. enters the chamber 60b, traverses the porous wall of the tube 66 equipped with its internal 70 and external 72 membranes and supplies the culture medium 9 of the cells with fresh medium and then issues into the internal chamber 62a. The passage of the nutrient medium through the first porous barrier (tube 66+ membranes) is ensured by means of an overpressure of the nutrient medium compared with the culture medium.

To this end the bioreactor 14 is equipped with an external pipe 82 linking the internal chamber 60a to the internal chamber 62a. This pipe 82 is equipped with a valve 84 making it possible to modify the pressure drop in said pipe 82 in order to increase the pressure in the first tubes 66. When the liquid passes into the second tubular barrier constituted by the tube 68 and its internal and external membranes 70 and 72, the liquid is charged with liquid depleted in nutrient elements of the cells and returns to the reactor or mixing chamber 18 for recharging with nutrient elements.

The reactor 14 also has another porous, mineral tube 86, which is in particular made from porous carbon and is isolated from the two enclosures 60 and 62 and consequently the chambers 60a, 60b, 62a and 62b and which is used for the extraction of the substances or metabolites produced by the cells of the culture medium 9. The end of the tube not used for the extraction of the metabolites is equipped for this purpose with a sealing plug 88.

This porous tube 86 is equipped with an external, microporous, filtering membrane 90, in particular of zirconia, which makes it possible to sample the metabolites produced by the cells cultured in the culture medium 9 and surrounding the different tubes 66, 68, 86. This membrane 90 has a cutoff threshold of the same order of magnitude as that of the internal, filtering membrane 70, i.e. approximately 0.08 micrometer. This microporous membrane 90 is impermeable to the cells, but is permeable to the macromolecules, which can thus be drawn off during the continuous operation of the bioreactor. The sampling of the culture medium containing proteins and metabolites can take place sequentially in the buffer tank 48.

According to the invention, the cylindrical sleeve 74 is surrounded by a second, external, cylindrical sleeve 92 in order to form an annular space 94 between the two sleeves in which can circulate a liquid ensuring the temperature regulation of the culture medium 9.

Silicone seals 96 are provided in the partitions 74, 76 and walls 78, 80 of the enclosures 60, 62 respectively. The enclosures 60, 62, as well as the internal sleeve 64 are preferably made from stainless steel. Thus, the animal cells of the culture medium are only in contact with the stainless steel, the silicone of the seals and the material forming the mineral barriers (tube+membranes).

The rotation of the bioreactor 14 about its longitudinal axis can be ensured by any random hydraulic, pneumatic or mechanical system and e.g. with the aid of a pinion 98 acting on a toothed ring 100 mounted on the enclosure 60. In order to support the bioreactor 14 whilst still permitting its rotation, it is equipped with a support 102 having a roller system 104.

The aforementioned bioreactor only has two tubes 66 and 68 for the flow of the nutrient medium and one tube for the extraction of the metabolites and in particular the monoclonal antibodies.

This representation of the three tubes only has been for simplification reasons. Thus, in practice, a plurality of tubes, e.g. 5, 7, 19, 37 and even more tubes arranged in regular manner within the bioreactor are used. In order to ensure the alternating connection of the internal and external chambers of the two enclosures 60 and 62, the number of tubes 66 and the number of tubes 68 must be equal.

The most favourable arrangement from the homogeneity standpoint is an equilateral triangular spacing for the tubes, although an arrangement such as a square, regular pentagon or others can be envisaged.

The performance characteristics of the bioreactor according to the invention improve with an increase in the number of porous tubes such as 66 and 68 for supplying the nutrient medium and provided that the number of extraction tubes does not increase excessively.

The form and operation of the apparatus according to the invention have been selected so as to permit a continuous, long-term production of metabolites even with a culture medium which is not free from proteins. The limitation of the clogging of the porous barriers (membranes+tube) is obtained as a result of a careful choice of the microporous zirconia membranes described hereinbefore, but also by limiting the transfer pressures between the different tubes.

We claim:

1. Bioreactor for animal cell culturing comprising: a cellular culture chamber (65), formed by a sleeve (64) and facing walls (78, 80) of two enclosures, respectively, an intake enclosure (60) and a discharge enclosure (62), said chamber containing the cells and a culture medium containing proteins; each enclosure being provided with an internal partition (74, 76) subdividing said each enclosure into a first (60a, 62a) and a second (60b, 62b) respectively internal and external chambers;

at least one first porous mineral tube (66) connecting the external chamber (60b) of the intake enclosure (60) to the internal chamber (62a) of the discharge enclosure (62) and traversing said culture chamber (65) for supplying nutrient medium (19) to the culture medium (9), said first porous mineral tube (66) having on its inner face a first microporous filtering membrane (70) which prevents the passage of macromolecules of the nutrient medium (19) having a high molecular weight, and on its outer face a second microfiltering membrane (72) permitting the passage of low molecular weight molecules and serving as a barrier for the cells and the proteins present in the cellular culture chamber;

at least one second porous mineral tube (68) connecting the internal chamber (60a) of the intake enclosure (60) to the external chamber (62b) of the discharge enclosure (62), while traversing the cellular culture chamber (65), said second porous mineral tube having a porosity which permits the passage of low molecular weight metabolites from the cellular culture chamber into said second tube (68) having on its outer and inner faces, respectively, said first and second membranes (70, 72);

a connecting pipe (82) between the two internal chambers (60a, 62a) of the intake and discharge enclosures, having valve means to produce a pressure drop between said two internal chambers for a better material transfer through the first (66) and second (68) porous mineral tubes and which produces a flow in the same direction of the nutrient medium through said first and second porous mineral tubes, for improving the homogeneity of the cell medium in the bioreactor.

2. Bioreactor according to claim 1, wherein said valve means comprises a regulating valve means (84) for adjusting and checking the pressure drop in said pipe (82) and for thus obtaining a very substantially constant transfer over an entire length of said first (66) and second (68) porous mineral tubes.

3. Bioreactor according to claim 1, further comprises at least one additional porous mineral tube (86) which is not in flow communication with the two enclosures (60, 62), said additional tube traverses said culture chamber (65) and has its outer face covered by a third microporous filtering membrane (90), which is impermeable to the cells and of high molecular weight produced in the cellular culture chamber (65).

4. Bioreactor according to claim 3, wherein the first (70), second (72) and third (90) membranes are mineral membranes.

5. Bioreactor according to claim 3, wherein the first, second and third membranes (70, 72, 90) are made from a material chosen from the group consisting of $Al_2O_3$, $TiO_2$ and $ZrO_2$.

6. Bioreactor according to claim 1, wherein the second filtering membrane (72) has a cutoff threshold below that of the first filtering membrane (70).

7. Bioreactor according to claim 1, wherein the first and second tubes (66, 68, 86) are made from porous carbon.

8. Bioreactor according to claim 3, wherein the third filtering membrane (90) has a cutoff threshold close to that of the first membrane (70).

9. Bioreactor according to claim 1, wherein an outer sleeve (92) surrounding the sleeve forming an annular space (94) therebetween in which a fluid for regulating the temperature of the culture medium flows.

10. Bioreactor according to claim 1, wherein means (34) are provided for periodically reversing the flow direction of the nutrient medium (19) in the first tube (66, 68).

11. Bioreactor according to claim 1, further comprising means (98, 100) for bringing about an alternate rotation thereof by approximately 180° about a longitudinal axis (15).

12. Apparatus for the continuous culture of animal cells comprising a mixing chamber (18) for checking and preparing the nutrient medium connected to the bioreactor (14) of claim 1, by flexible pipes (16, 32) and further comprising means (48, 46, 42, 52) for the continuous extraction of substances produced by the cells, said extraction means being connected to the bioreactor (14) by flexible pipes (40).

13. Apparatus for the continuous culture of animal cells comprising a mixing chamber (18) for checking and preparing the nutrient medium and connected to the bioreactor (14) of claim 1, by flexible pipes (16, 32) and further comprising means (48, 46, 42, 52) for the sequential extraction of substances produced by the cells, said extraction means being connected to the bioreactor (14) by flexible pipes (40).

* * * * *

UNITED STATES PATENT AND TRADEMARK OFFICE
CERTIFICATE OF CORRECTION

PATENT NO. : 5,064,764
DATED : November 12, 1991
INVENTOR(S) : Bernard Besnainou et al.

It is certified that error appears in the above-identified patent and that said Letters Patent is hereby corrected as shown below:

On the face of the patent, Section [75], first Inventor, "Besnainon"
    should be --Besnainou--;

In the Abstract, line 2, "tube" should be --tubes--;

Column 8, line 15, after "and" add --macromolecules--;

Column 8, line 15, delete "produced";

Column 8, line 34, after "sleeve" insert --for--.

Signed and Sealed this

Eighth Day of June, 1993

Attest:

MICHAEL K. KIRK

*Attesting Officer*   *Acting Commissioner of Patents and Trademarks*